United States Patent
Kojima et al.

(10) Patent No.: US 11,529,649 B2
(45) Date of Patent: Dec. 20, 2022

(54) PIEZOELECTRIC FILM, PIEZOELECTRIC MODULE, AND METHOD OF MANUFACTURING PIEZOELECTRIC FILM

(71) Applicant: Seiko Epson Corporation, Tokyo (JP)

(72) Inventors: Chikara Kojima, Matsumoto (JP); Hironori Suzuki, Chino (JP); Eiji Osawa, Chino (JP); Koji Ohashi, Matsumoto (JP)

(73) Assignee: SEIKO EPSON CORPORATION

( * ) Notice: Subject to any disclaimer, the term of this patent is extended or adjusted under 35 U.S.C. 154(b) by 834 days.

(21) Appl. No.: 16/222,100

(22) Filed: Dec. 17, 2018

(65) Prior Publication Data

US 2019/0184426 A1     Jun. 20, 2019

(30) Foreign Application Priority Data

Dec. 18, 2017 (JP) .............................. JP2017-241520

(51) Int. Cl.
| | |
|---|---|
| *B06B 1/06* | (2006.01) |
| *B06B 1/02* | (2006.01) |
| *H01L 41/04* | (2006.01) |
| *H01L 41/08* | (2006.01) |
| *H01L 41/312* | (2013.01) |
| *H01L 41/331* | (2013.01) |
| *H01L 41/332* | (2013.01) |

(Continued)

(52) U.S. Cl.
CPC .......... *B06B 1/0622* (2013.01); *A61B 8/4488* (2013.01); *B06B 1/0207* (2013.01); *G10K 9/125* (2013.01); *H01L 41/042* (2013.01); *H01L 41/081* (2013.01); *H01L 41/312* (2013.01); *H01L 41/331* (2013.01); *H01L 41/332* (2013.01)

(58) Field of Classification Search
CPC ... B06B 1/0207; B06B 1/0622; A61B 8/4488; G10K 9/125; H01L 41/042; H01L 41/081; H01L 41/312; H01L 41/331; H01L 41/332
USPC ....................................................... 310/317
See application file for complete search history.

(56) References Cited

U.S. PATENT DOCUMENTS

| | | | |
|---|---|---|---|
| 2014/0071204 A1* | 3/2014 | Kusunoki | ............ B41J 2/14233 347/50 |
| 2015/0158052 A1 | 6/2015 | Latev et al. | |

(Continued)

FOREIGN PATENT DOCUMENTS

| | | |
|---|---|---|
| JP | 2004-304193 A | 10/2004 |
| JP | 2011-103591 A | 5/2011 |

(Continued)

*Primary Examiner* — Emily P Pham
*Assistant Examiner* — Monica Mata
(74) *Attorney, Agent, or Firm* — Harness, Dickey & Pierce, P.L.C.

(57) ABSTRACT

A piezoelectric film includes a substrate having flexibility, and at least two piezoelectric elements provided to the substrate so as to be arranged at intervals of a first dimension along a first direction, the piezoelectric elements are each configured by stacking a first electrode film, a piezoelectric film made of an inorganic material, and a second electrode film along a thickness direction of the substrate, and an area between the piezoelectric elements adjacent to each other along the first direction forms a vibrational region which can be displaced in the thickness direction.

13 Claims, 10 Drawing Sheets

(51) Int. Cl.
*A61B 8/00* (2006.01)
*G10K 9/125* (2006.01)

(56) References Cited

U.S. PATENT DOCUMENTS

2017/0201234 A1 7/2017 Jager et al.
2017/0253039 A1* 9/2017 Kimura ................ H01L 41/083

FOREIGN PATENT DOCUMENTS

| | | |
|---|---|---|
| JP | 2013-218259 A | 10/2013 |
| JP | 2017-500804 A | 1/2017 |
| JP | 2017-526202 A | 9/2017 |

* cited by examiner

PIEZOELECTRIC FILM, PIEZOELECTRIC MODULE, AND METHOD OF MANUFACTURING PIEZOELECTRIC FILM

BACKGROUND

1. Technical Field

The present invention relates to a piezoelectric film, a piezoelectric module, and a method of manufacturing a piezoelectric film.

2. Related Art

In the past, there has been known a piezoelectric film formed of a piezoelectric material having flexibility (a flexible property) (see, e.g., JP-A-2004-304193 (Document 1)). The piezoelectric film described in Document uses vinylidene fluoride (PVDF) as the piezoelectric material. In such a piezoelectric film, it is possible to wind the piezoelectric film on an outer circumferential surface of an object having a columnar shape to mount the piezoelectric film on the outer circumferential surface thereof to thereby perform transmission and reception of an ultrasonic wave to and from the object.

However, the piezoelectric film using an organic piezoelectric material such as PVDF as described in Document 1 mentioned above is superior in flexibility, but has a problem that the piezoelectric characteristic is low compared to a piezoelectric body formed of an inorganic material such as PZT. For example, the piezoelectric strain constant of PVDF is roughly 1/5 of that of PZT. Further, the organic piezoelectric material is low in Curie point. For example, the Curie point of PZT is about 300° C. on the one hand, and that of PVDF is about 50° C. in the other hand. Therefore, there is a problem that the purpose of use of the organic piezoelectric material is limited.

In contrast, in the case of outputting the ultrasonic wave with the piezoelectric film using the inorganic material as the piezoelectric body, a method (thickness vibration) of vibrating the piezoelectric film in the thickness direction, and a method (flexural vibration) of displacing the vibrating plate using a displacement of PZT have been used.

However, the resonance frequency of the thickness vibration is determined by the film thickness of the piezoelectric film, and the lower the frequency becomes, the thicker the film thickness is required to be made. In this case, if the thickness dimension of the piezoelectric film is made large in order to output a low-frequency ultrasonic wave, the rigidity of the piezoelectric film also becomes high, and there is a problem that the flexibility of the piezoelectric film is deteriorated.

Further, in the case of outputting the ultrasonic wave using the flexural vibration, it is necessary to surround an area to be vibrated of the vibrating plate with a support body having rigidity to thereby form a cavity. Therefore, since the configuration requires the support body, there is a problem that the flexibility of the piezoelectric film is deteriorated.

SUMMARY

An advantage of some aspects of the invention is to provide a piezoelectric film, a piezoelectric module high in piezoelectric characteristics and heat resistance, and good in flexibility, and a method of manufacturing the piezoelectric film.

A piezoelectric film according to an application example of the invention includes a substrate having flexibility, and at least two piezoelectric elements provided to the substrate so as to be arranged at intervals of a first dimension along a first direction, the piezoelectric elements are each configured by stacking a first electrode film, a piezoelectric film made of an inorganic material, and a second electrode film along a thickness direction of the substrate, and an area of the substrate between the piezoelectric elements adjacent to each other along the first direction forms a vibrational region which can be displaced in the thickness direction.

In the application example, the plurality of piezoelectric elements arranged at the intervals of the first dimension along the first direction are disposed on the substrate having flexibility, and the piezoelectric elements are each constituted by the first electrode film, the piezoelectric film made of the inorganic material, and the second electrode film. In such a piezoelectric film, when a drive signal is input to the piezoelectric elements, it is possible to generate a vibration using the piezoelectric elements as nodes and the vibrational regions as antinodes, and it becomes possible to output an ultrasonic wave due to the vibrations of the vibrational regions. Therefore, it is possible to obtain the piezoelectric film which does not require such a support body as in the related art, which can lower the rigidity of the piezoelectric elements since there is no need to change the thickness dimension of the piezoelectric elements in accordance with the frequency, and which is good in flexibility.

Further, the piezoelectric film according to the application example uses the piezoelectric film made of the inorganic material, and is therefore higher in piezoelectric characteristics, and higher in Curie point compared to the case of using the piezoelectric film made of an organic material. Therefore, even in the case in which, for example, the ultrasonic wave is transmitted from the piezoelectric film to the inside of a high-temperature pipe, it becomes possible to wind the piezoelectric film around the pipe in good condition, and at the same time, it becomes possible to transmit the ultrasonic wave high in sound pressure to the inside of the pipe even in the high-temperature circumstances.

In other words, it is possible to provide the piezoelectric film high in piezoelectric characteristics and heat resistance, and also superior in flexibility.

In the piezoelectric film according to the application example, it is preferable that a slit groove having a predetermined depth dimension along the thickness direction is disposed at a center in the first direction of the vibrational region of the substrate along a second direction crossing the first direction.

As described above, in the piezoelectric film according to the application example, when the drive signal is input to each of the piezoelectric elements, there is generated the vibration using the piezoelectric elements as the nodes and the vibrational region between the piezoelectric elements adjacent to each other as the antinode. In the application example with the configuration described above, since the slit groove along the second direction crossing the first direction is disposed at the center in the first direction of each of the vibrational regions, it is possible to enlarge the amplitude of the vibration in the first direction in the vibrational region. Thus, it becomes possible to output the ultrasonic wave high in sound pressure.

In the piezoelectric film according to the application example, it is preferable that the three or more piezoelectric elements are arranged along the first direction at intervals of the first dimension.

In the application example with this configuration, the three or more piezoelectric elements are arranged at regular intervals along the first direction. As described above, in the piezoelectric film according to the application example, when inputting the drive signal to the piezoelectric elements, the vibrational region between the piezoelectric elements adjacent to each other vibrates as the antinode to output the ultrasonic wave. Therefore, by arranging the three or more piezoelectric elements at regular intervals, the ultrasonic waves having the same frequency are output from the respective vibrational regions as a result, and it is possible to transmit the ultrasonic wave high in sound pressure with the predetermined frequency.

In the piezoelectric film according to the application example, it is preferable that defining a plurality of the piezoelectric elements arranged along the first direction as an element column, a plurality of the element columns is arranged along a second direction crossing the first direction, the piezoelectric elements in the element column disposed (i+1)-th in the second direction, in the projection view along the second direction, overlap the respective vibrational regions disposed between the piezoelectric elements in the element column disposed i-th in the second direction, and the piezoelectric elements in the element column disposed (i+2)-th in the second direction, in the projection view from the second direction, overlap the respective piezoelectric elements in the element column disposed i-th in the second direction.

In the application example with this configuration, the two-dimensional array structure in which the piezoelectric elements are arranged along the first direction and the second direction is provided. Further, the (i+1)-th piezoelectric elements are disposed at the positions overlapping the i-th vibrational regions in a projection view from the second direction. In other words, in the application example with the configuration described above, the configuration in which the piezoelectric elements are arranged in a staggered manner (forming a roughly zigzag structure) is provided. In such a configuration, it is possible to largely vibrate the vibrational regions due to the piezoelectric element array having the piezoelectric elements arranged in the two-dimensional array structure, and it becomes possible to output the ultrasonic wave high in sound pressure in a broad range.

In the piezoelectric film according to the application example, it is preferable that the i-th piezoelectric elements in the second direction and the (i+2)-th piezoelectric elements in the second direction are arranged with a distance of the first dimension.

The ultrasonic wave output in such a piezoelectric film as described above is determined in frequency in accordance with the dimension in the short axis direction of the vibrational region. In the application with the configuration described above, the dimension along the first direction of the vibrational region between the piezoelectric elements arranged along the first direction and the dimension along the second direction of the vibrational region between the piezoelectric elements arranged along the second direction become the same dimension (the first dimension). Therefore, the ultrasonic waves having the same frequency corresponding to the first dimension are output from the respective vibrational regions as a result, and it is possible to output the ultrasonic wave having the predetermined frequency on high power.

In the piezoelectric film according to the application example, it is preferable that the substrate includes a first substrate made of resin, and a second substrate formed of an oxide film stacked on the first substrate, the piezoelectric elements are provided to the second substrate, and a thickness in the thickness direction of the second substrate and the piezoelectric elements is equal to or smaller than 5 µm.

In the application example with this configuration, the substrate is constituted by the first substrate made of resin and the second substrate made of the oxide film, and the total thickness dimension of the second substrate and the piezoelectric element is equal to or smaller than 5 µm. In such a structure, the piezoelectric film becomes easier to bend, and it is possible to achieve a further improvement of flexibility.

In the piezoelectric film according to the application example, it is preferable that the first electrode films of a plurality of the piezoelectric elements are connected to each other, and the second electrode films of a plurality of the piezoelectric elements are connected to each other.

In the application example, in the case of outputting the ultrasonic wave from the piezoelectric film, as described above, the predetermined drive signal is input to the piezoelectric elements at the same time to vibrate the vibrational regions. Here, in the application example with the configuration described above, the first electrode films of the respective piezoelectric elements are connected to each other, and the second electrode films thereof are connected to each other. Therefore, there is no need to connect signal lines to the first electrode film and the second electrode film of each of the piezoelectric elements, and it is possible to simplify the wiring structure.

A piezoelectric module according to an application example of the invention includes the piezoelectric film, and a control section adapted to control the piezoelectric film.

In the application example, as described above, it is possible to provide the piezoelectric film high in piezoelectric characteristics and heat resistance, and also superior in flexibility. Further, by controlling the piezoelectric film with the control section, it is possible to transmit the ultrasonic wave to the object at high sound pressure.

In the piezoelectric module according to the application example, it is preferable that the control section inputs a predetermined drive signal to a plurality of the piezoelectric elements at the same timing.

It is also possible to adopt a configuration in which the first electrode film and the second electrode film of each of the piezoelectric elements are each provided with an independent signal line and an independent terminal section as the piezoelectric film, and in this case, the same drive signal is input from the control section to the terminal sections at the same time. Thus, it becomes possible to excite the vibration mode using piezoelectric elements as the nodes and the vibrational region as the antinode to output the ultrasonic wave having the predetermined frequency.

A method of manufacturing a piezoelectric film according to an application example of the invention is a method of manufacturing a piezoelectric film including a substrate having flexibility, and at least two piezoelectric elements provided to the substrate so as to be arranged at intervals of a first dimension along a first direction, the method including the steps of forming a plurality of the piezoelectric elements each having a first electrode film, a piezoelectric film made of an inorganic material, and a second electrode film stacked on one another on a first platform having a first surface and a second surface on an opposite side to the first surface at intervals of the first dimension along the first direction, forming a resist for covering a plurality of the piezoelectric elements on the first surface of the first platform, bonding a second platform to a surface on an opposite side to the first platform of the resist, removing the first platform from the second surface, forming a substrate having flexibility in a part where the first platform is removed in the removing the first platform, and removing the resist to separate the second platform.

In the application example, the piezoelectric elements arranged at intervals of the first dimension along the first direction are formed on the first platform due to the step of forming a plurality of the piezoelectric elements. Then, by forming the resist due to the step of forming the resist, the piezoelectric elements are made to be held by the resist, and by bonding the second platform to the resist due to the step of bonding the second platform, there is formed a configuration in which the positions of the piezoelectric elements are kept by the second platform and the resist even in the case in which the first platform is removed in the step of removing the first platform. Then, by forming the substrate having flexibility in the part where the first platform is removed in the step of forming the substrate having flexibility, there is provided the configuration in which the piezoelectric elements are held by the substrate. Therefore, by removing the resist to separate the second platform in the step of removing the resist to separate the second platform, it becomes possible to manufacture such a piezoelectric film as described above in which the plurality of piezoelectric elements is arranged at regular intervals along the first direction on the substrate having flexibility.

BRIEF DESCRIPTION OF THE DRAWINGS

The invention will be described with reference to the accompanying drawings, wherein like numbers reference like elements.

DESCRIPTION OF AN EXEMPLARY EMBODIMENT

A piezoelectric module as an embodiment according to the invention will hereinafter be described.

Figure 1:
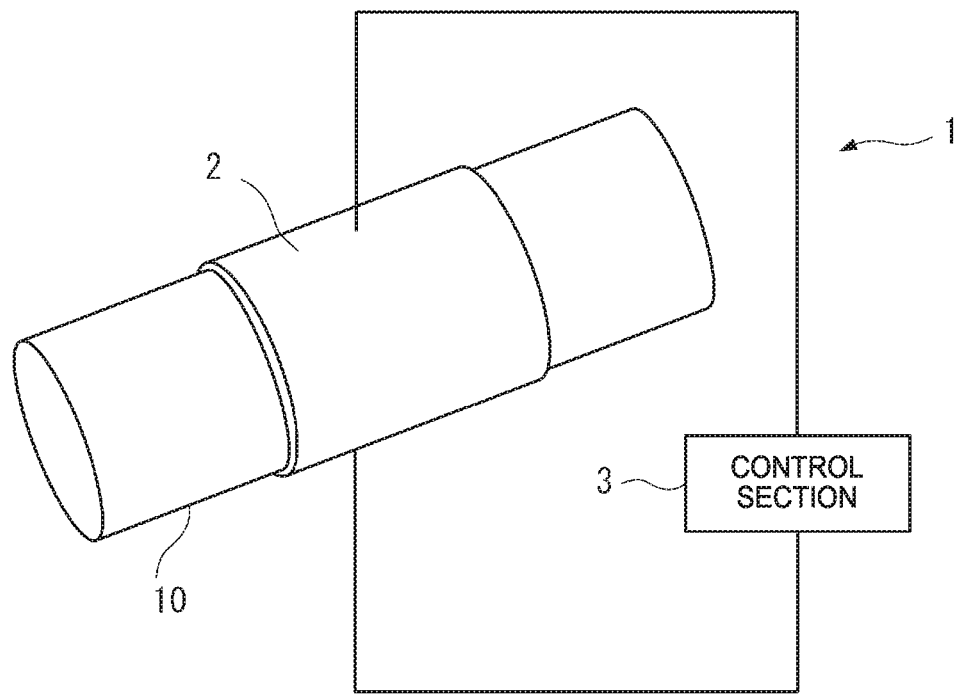
FIG. 1 is a diagram showing a schematic configuration of a piezoelectric module according to an embodiment of the invention.

FIG. 1 is a diagram showing a schematic configuration of the piezoelectric module 1 according to the present embodiment.

As shown in FIG. 1, the piezoelectric module 1 according to the present embodiment is provided with a piezoelectric film 2, and a control section 3 for controlling drive of the piezoelectric film 2.

The piezoelectric film 2 is what is used while being attached to an object 10, and can be deformed in accordance with the shape of the object 10. In the case in which the object 10 is a pipe or the like having a cylindrical shape, it becomes possible to wind the piezoelectric film 2 around the object 10. Then, by controlling the piezoelectric film with the control section 3, it is possible to transmit the ultrasonic wave from the piezoelectric film 2 to the object 10. By using the piezoelectric module 1, it becomes possible to perform a variety of processes such as an internal inspection of the object or a formation of an internal tomographic image using the transmission and reception of the ultrasonic wave.

Configuration of Piezoelectric Film 2

Figure 2:
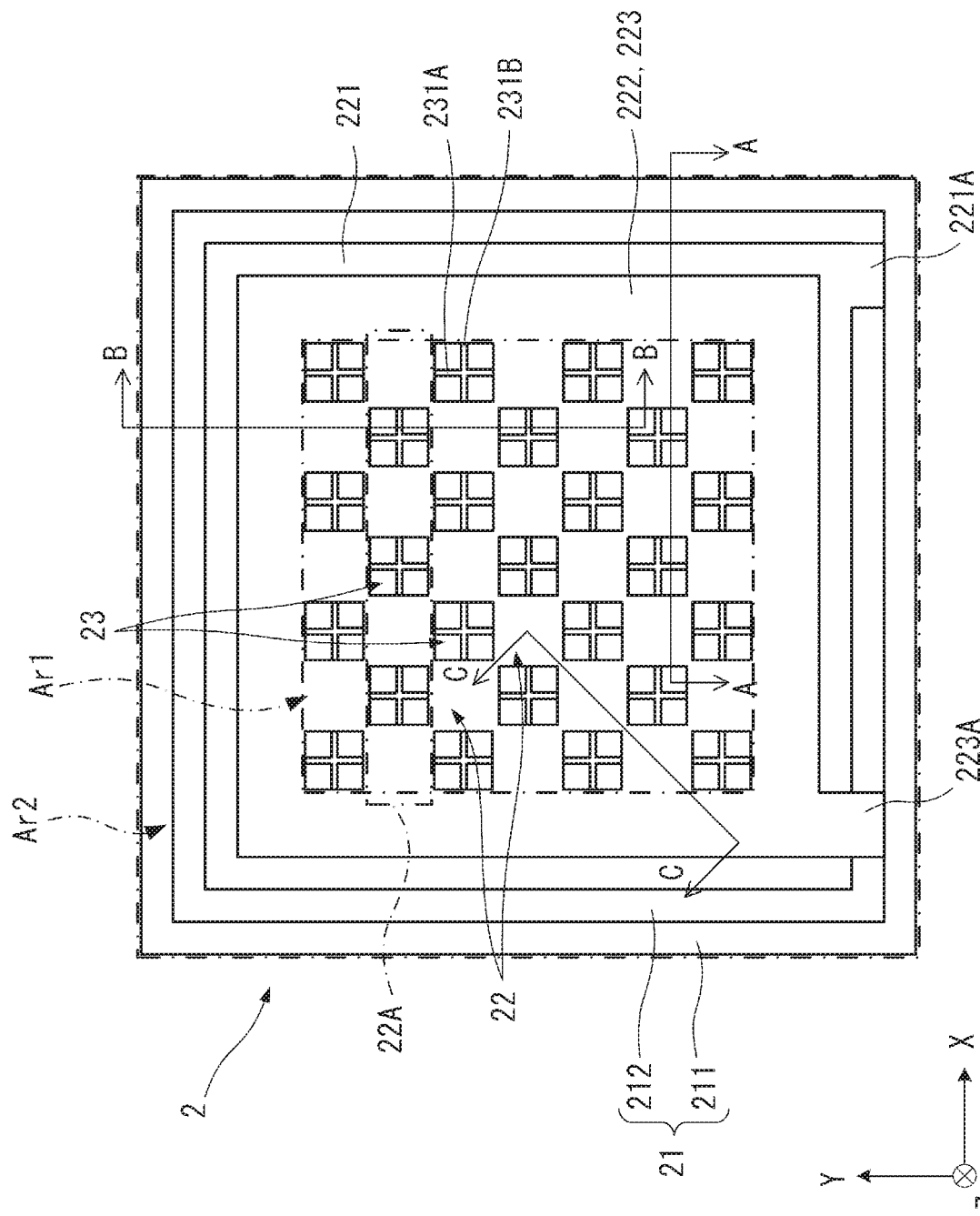
FIG. 2 is a plan view showing a schematic configuration of a piezoelectric film according to the embodiment.
Figure 3:
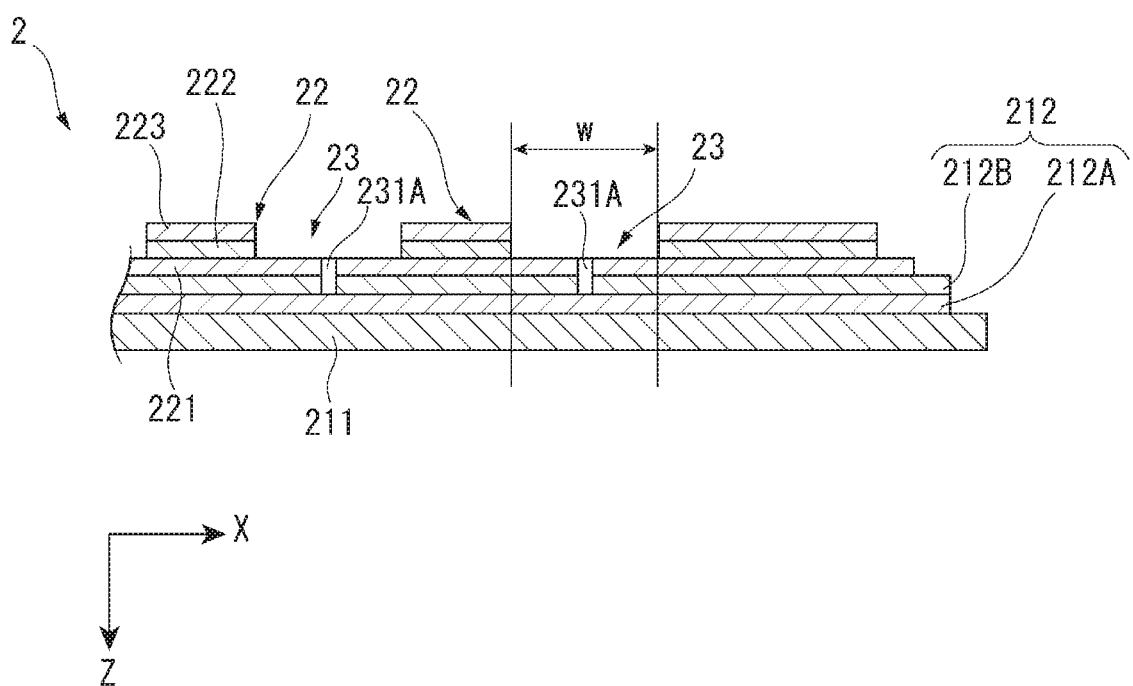
FIG. 3 is a cross-sectional view of the piezoelectric film in the case of cutting the piezoelectric film shown in FIG. 2 along the line A-A.

FIG. 2 is a plan view showing a schematic configuration of the piezoelectric film 2 constituting the piezoelectric module 1. FIG. 3 is a cross-sectional view of the piezoelectric film 2 in the case of cutting the piezoelectric film 2 shown in FIG. 2 along the line A-A.

Figure 4:
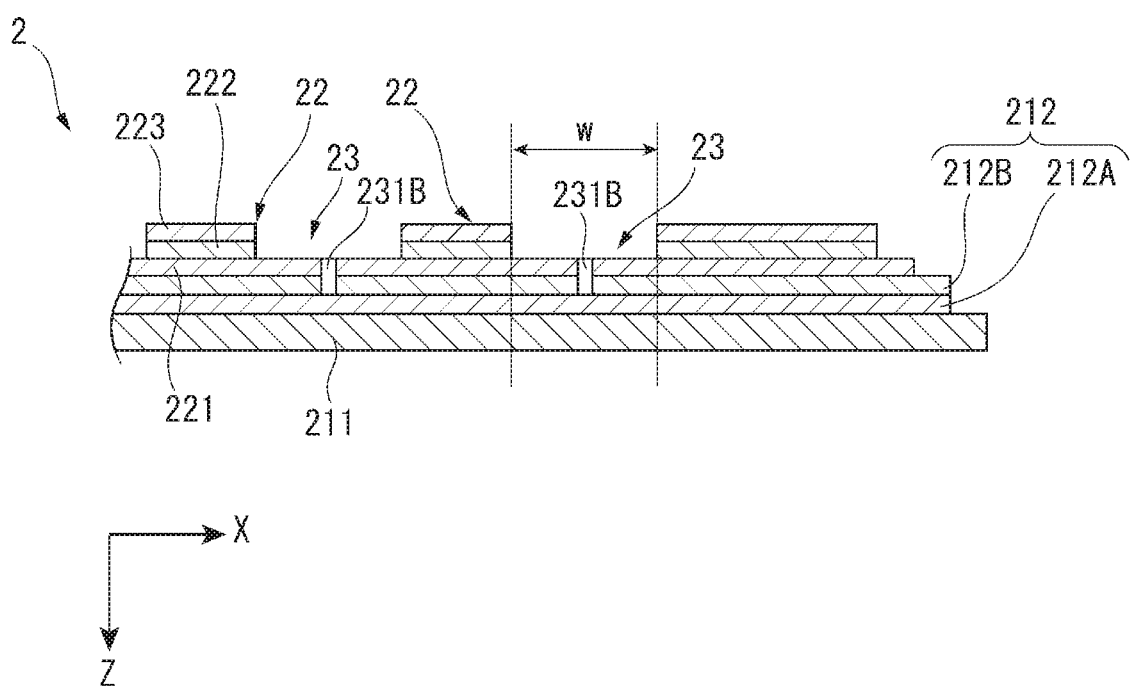
FIG. 4 is a cross-sectional view of the piezoelectric film in the case of cutting the piezoelectric film shown in FIG. 2 along the line B-B.

FIG. 4 is a cross-sectional view of the piezoelectric film 2 in the case of cutting the piezoelectric film 2 shown in FIG. 2 along the line B-B.

Figure 5:
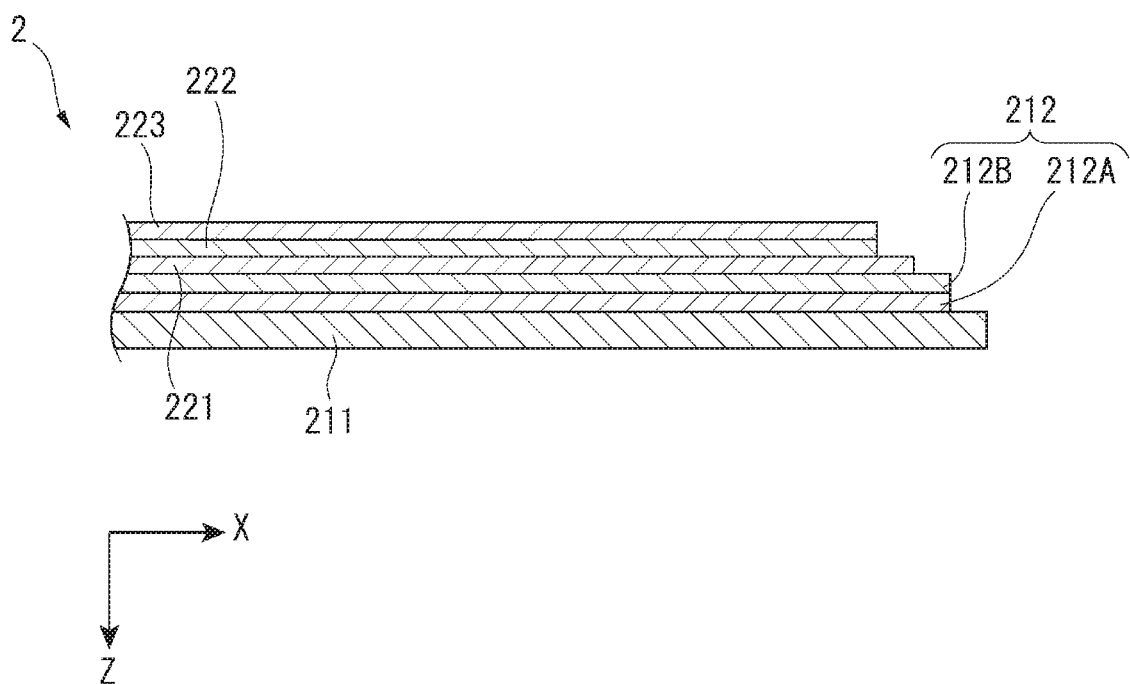
FIG. 5 is a cross-sectional view of the piezoelectric film in the case of cutting the piezoelectric film shown in FIG. 2 along the line C-C.

FIG. 5 is a cross-sectional view of the piezoelectric film 2 in the case of cutting the piezoelectric film 2 along the line C-C. It should be noted that in FIG. 2, the number of piezoelectric elements 22 arranged is reduced for the sake of convenience of explanation, but in reality, there are arranged a larger number of piezoelectric elements 22.

As shown in FIG. 2, the piezoelectric film 2 is configured including a substrate 21 having flexibility, and the piezoelectric elements 22 disposed on the substrate 21. It should be noted that as a preparation for the following explanation, the thickness direction of the substrate 21 in the state in which the substrate 21 does not vibrate is defined as a Z direction, a direction perpendicular to the Z direction is defined as an X direction (a first direction), and a direction perpendicular to the Z direction and crossing (e.g., perpendicular to) the X direction is defined as a Y direction (a second direction).

The substrate 21 is configured including a first substrate 211 and a second substrate 212.

The first substrate 211 is a plastic flexible substrate formed of a resin material such as polyimide.

The second substrate 212 is a film member which is stacked on the first substrate, and which is formed of a metal-oxide film. In the present embodiment, the second substrate 212 is formed of a stacked body having an $SiO_2$ layer 212A and a $ZrO_2$ layer 212B stacked in this order from the first substrate 211 side.

Such a substrate 21 has flexibility, and can be curved or bent in accordance with the shape of the object 10.

Further, as shown in FIG. 2, the piezoelectric film 2 is provided with a drive area Ar1 disposed in a central part of the piezoelectric film 2 and an outer peripheral area Ar2 surrounding the drive area Ar1 in a planar view viewed from the Z direction.

In the drive area Ar1, there is disposed a plurality of piezoelectric elements 22 arranged to form a two-dimensional array structure, and the drive area Ar1 is driven under the control by the control section 3. The outer peripheral area Ar2 surrounds the outer periphery of the drive area Ar1, and functions as a fixed end in the case of driving (vibrating) the drive area Ar1. Further, in the outer peripheral area Ar2, there are disposed terminal sections 221A, 223A to which drive signals for driving the drive area Ar1 are input.

The piezoelectric elements 22 disposed in the drive area Ar1 will be described.

The piezoelectric elements 22 are disposed on the second substrate 212 of the substrate 21, and inside the drive area Ar1. As shown in FIG. 2, these piezoelectric elements 22 are arranged in a roughly zigzag arrangement (in a zigzag manner). In other words, the piezoelectric elements 22 have a configuration in which the piezoelectric elements 22 are arranged along the X direction at regular intervals of predetermined first dimensions w to thereby constitute an element column 22A extending along the X direction, and the element columns 22A are arranged in the Y direction. It should be noted that the area between the piezoelectric elements 22 adjacent to each other in the substrate 21 constitutes a vibrational region 23, and forms an area largely displaced in the case of driving the piezoelectric film 2.

Further, in the present embodiment, the piezoelectric elements 22 in the element columns 22A adjacent in the Y direction to each other are arranged in a zigzag manner. In other words, in a projection view of the piezoelectric film 2 from the Y direction, the piezoelectric elements 22 in the element column 22A disposed (i+1)-th in the Y direction do not overlap the piezoelectric elements 22 in the element column 22A disposed i-th but overlap the vibrational regions 23 in the element column 22A disposed i-th to form the zigzag arrangement (a roughly zigzag shape). Further, the arrangement positions in the X direction of the piezoelectric elements 22 in the element column 22A disposed (i+2)-th in the Y direction are the same as the arrangement positions in the X direction of the piezoelectric elements 22 in the element column 22A disposed i-th. Therefore, in the projection view of the piezoelectric film 2 viewed from the Y direction, the piezoelectric elements 22 in the element column 22A disposed (i+2)-th in the Y direction overlap the piezoelectric elements 22 in the element column 22A disposed i-th.

In other words, in the present embodiment, there is provided the two-dimensional array structure in which the piezoelectric elements 22 and the vibrational regions 23 are alternately arranged in each of the X direction and the Y direction.

A specific configuration of the piezoelectric elements 22 will be described.

As shown in FIG. 3 and FIG. 4, the piezoelectric elements 22 are each formed of a stacked body having a first electrode film 221, a piezoelectric film 222 and a second electrode film 223 stacked in this order from the second substrate 212.

The first electrode film 221 is formed of a conductive material. As the conductive material, it is possible to use metal such as Ti, Pt, Ta, Ir, Sr, In, Sn, Au, Al, Fe, Cr, Ni, or Cu, or electrically conductive oxide represented by lanthanum-nickel oxide (LNO) or the like alone, or a material obtained by combining or stacking two or more of these materials. In the present embodiment, the first electrode film 221 is formed of a stacked body of Pt, Ti, Ir and Ti.

As shown in FIG. 2 through FIG. 5, the first electrode film 221 is disposed on the second substrate 212 of the substrate 21 from the drive area Ar1 to the outer peripheral area Ar2 so as to cover the entire area of the drive area Ar1. Further, as shown in FIG. 2, a part of the first electrode film 221 disposed in the outer peripheral area Ar2 is disposed so as to extend to an outer peripheral end of the second substrate 212 to constitute the terminal section 221A. The terminal section 221A is connected to the control section 3 so that a voltage signal is input from the control section 3 to the terminal section 221A.

Therefore, there is provided the configuration in which the first electrode films 221 constituting the respective piezoelectric elements 22 are connected to each other.

The piezoelectric film 222 is formed of an inorganic piezoelectric material. For example, in the case of using a ferroelectric ceramics material as the inorganic piezoelectric material, the piezoelectric film 222 is formed of a crystal film (a perovskite-type crystal) of an oxide having a perovskite structure made of a ferroelectric ceramics material.

As the ferroelectric ceramics material, there can be used, for example, lead zirconate titanate (PZT), those obtained by adding a metal oxide such as niobium oxide, nickel oxide, or magnesium oxide to lead zirconate titanate (PZT), bismuth ferrate, barium titanate, and potassium sodium niobate. It should be noted that in the present embodiment, lead zirconate titanate (PZT) is used as the piezoelectric film 222.

The piezoelectric films 222 are arranged to have the two-dimensional array structure in such a roughly zigzag structure as described above in the drive area Ar1. Here, as shown in FIG. 2, the piezoelectric films 222 in the drive area Ar1 are each formed to have, for example, a roughly rectangular shape having a pair of sides parallel to the X direction and a pair of sides parallel to the Y direction. Further, the piezoelectric films 222 in the drive area Ar1 are each connected to the piezoelectric films 222 disposed in an oblique direction. Specifically, the piezoelectric film 222 of the piezoelectric element 22 disposed j-th in the X direction in the element column 22A disposed i-th in the Y direction is connected to the piezoelectric films 222 of the piezoelectric elements 22 disposed (j−1)-th and (j+1)-th in the X direction in the element columns 22A disposed (i+1)-th and (i−1)-th in the Y direction. It should be noted that $1<i<i_{max}$ is assumed defining $i_{max}$ as the number of the element columns 22A, and $1<j<j_{max}$ is assumed defining $j_{max}$ as the number of the piezoelectric elements 22 included in the element column 22A.

Further, in the outer peripheral area Ar2, the piezoelectric film 222 is formed to have a frame-like shape so as to surround the drive area Ar1. The piezoelectric films 222 of the piezoelectric elements 22 disposed in the outermost circumference (the boundary with the outer peripheral area Ar2) of the drive area Ar1 are connected to the piezoelectric film 222 in the outer peripheral area Ar2.

The second electrode film 223 is formed of a conductive material similarly to the first electrode film 221, and is constituted by, for example, a stacked body of Ti and Ir.

As shown in FIG. 2, the second electrode films 223 are formed on the piezoelectric films 222 at roughly the same positions as those of the piezoelectric films 222. Therefore, the first electrode film 221 and the second electrode film 223 are insulated from each other via the piezoelectric film 222.

As described above, the piezoelectric films 222 in the drive area Ar1 are respectively formed corresponding to the piezoelectric elements 22, and the piezoelectric films 222 disposed in the oblique direction are connected to each other. Therefore, the second electrode films 223 disposed on the piezoelectric films 222 also have the configuration in which the second electrode films 223 disposed in the oblique direction are connected to each other in a similar manner. Therefore, there is provided the configuration in which the second electrode films 223 of the respective piezoelectric elements 22 are connected to each other.

Further, as shown in FIG. 2, the piezoelectric film 222 and the second electrode film 223 are disposed so as to partially extend to the outer peripheral end of the second substrate 212 in the outer peripheral area Ar2 to constitute the terminal section 223A. The terminal section 223A is connected to the control section 3 so that a voltage signal is input from the control section 3 to the terminal section 223A.

Further, in the present embodiment, the second substrate 212, and the first electrode film 221, the piezoelectric film 222 and the second electrode film 223 constituting the piezoelectric element 22 are formed so that the sum of the thickness dimensions of the second substrate 212 and the piezoelectric element 22 is equal to or smaller than 5 μm. Thus, the deterioration of the flexibility of the substrate 21 is prevented.

Further, inside the drive area Ar1, in each of the vibrational regions 23 corresponding to the areas between the piezoelectric elements 22, there are disposed slit grooves 231A, 231B having a predetermined depth dimension.

Specifically, in the vibrational region 23 between the two piezoelectric elements 22 adjacent in the X direction to each other, the slit groove 231A extending along the Y direction is disposed at a position where the distances from the two piezoelectric elements 22 are equal to each other, namely the center in the X direction of the vibrational region 23.

Similarly, in the vibrational region 23 between the two piezoelectric elements 22 adjacent in the Y direction to each other, the slit groove 231B extending along the X direction is disposed at a position where the distances from the two piezoelectric elements 22 are equal to each other, namely the center in the Y direction of the vibrational region 23.

In other words, each of the vibrational regions 23 is provided with the slit grooves 231A, 231B forming a cross-like shape passing through the center of the vibrational region 23.

The slit grooves 231A, 231B are grooves formed for enlarging the displacement of the vibrational region 23 in the case of vibrating the vibrational region 23, and the groove thickness (the dimension in the Z direction) of the slit grooves 231A, 231B is not particularly limited. For example, the slit grooves 231A, 231B can also be formed so that the depth dimension of the slit grooves 231A, 231B is the depth from the first electrode film 221 to the $ZrO_2$ layer 212B of the second substrate 212, or can also be formed to a part of the first substrate 211. Further, the width dimensions of the slit grooves 231A, 231B are also not particularly limited.

Configuration of Control Section

The control section 3 is constituted by a circuit which is connected to the terminal sections 221A, 223A of the piezoelectric film 2, and which controls the drive of the piezoelectric film 2. As the control section 3, it is possible to adopt a personal computer or the like in which a driver circuit for the piezoelectric film 2 is installed, or a dedicated control device for controlling the drive of the piezoelectric film 2.

Specifically, the control section 3 outputs the drive signal for applying a periodic drive voltage to the terminal sections 221A, 223A of the piezoelectric film 2 to thereby make the piezoelectric film 2 output the ultrasonic wave to the object 10. Further, it is also possible for the control section 3 to obtain a reception signal in the case in which the piezoelectric elements 22 are displaced due to the ultrasonic wave received by the piezoelectric film 2 to thereby measure the distance from the piezoelectric film 2 to a reflection position of the ultrasonic wave.

Vibration of Piezoelectric Film 2

Then, the vibration generated in the drive area Ar1 of the piezoelectric film 2 in the case of applying the periodic drive voltage between the terminal section 221A and the terminal section 223A of such a piezoelectric film 2 as described above will be described.

Figure 6:
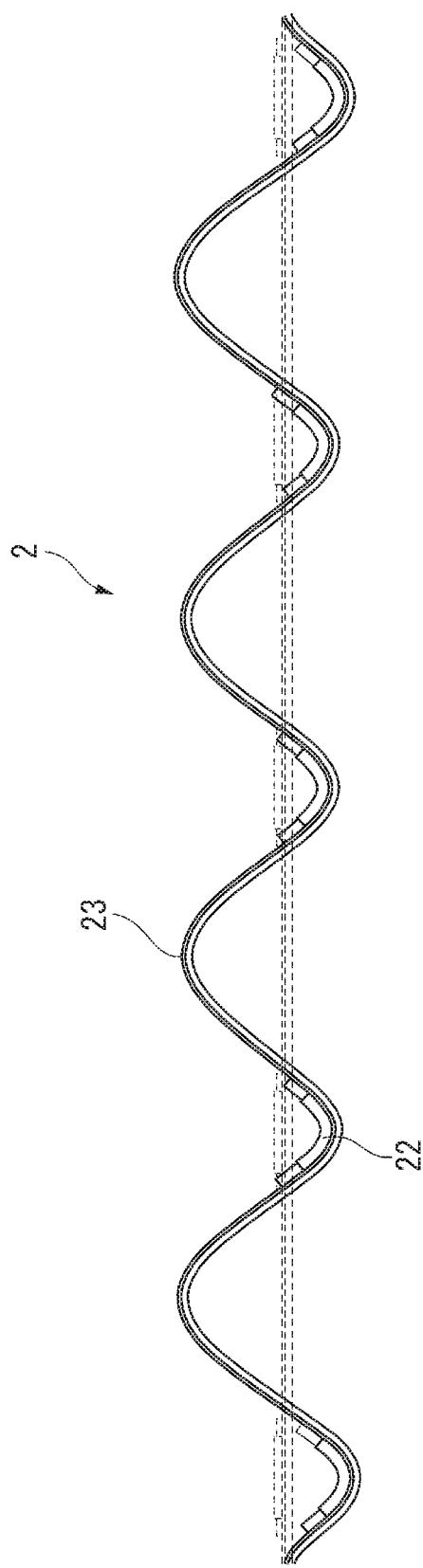
FIG. 6 is a cross-sectional view of the piezoelectric film for explaining a vibration generated in a drive area of the piezoelectric film.

FIG. 6 is a cross-sectional view of the piezoelectric film 2 for explaining the vibration generated in the drive area Ar1 of the piezoelectric film 2.

In the case of driving the piezoelectric film 2 according to the present embodiment to output the ultrasonic wave, the periodic drive voltage is applied to the terminal section 221A and the terminal section 223A. Thus, the drive voltage is applied between the first electrode film 221 and the second electrode film 223 of each of the piezoelectric elements 22 at the same time, and thus, the piezoelectric elements 22 are driven at the same time.

Thus, as shown in FIG. 6, the drive area Ar1 of the piezoelectric film 2 is resonated in the vibration mode having nodes in the vicinities of both end parts (the vicinity of the boundary between the piezoelectric element and the vibrational region 23) of the piezoelectric element 22 (the piezoelectric film 222) and an antinode in the vibrational region 23.

Figure 7:
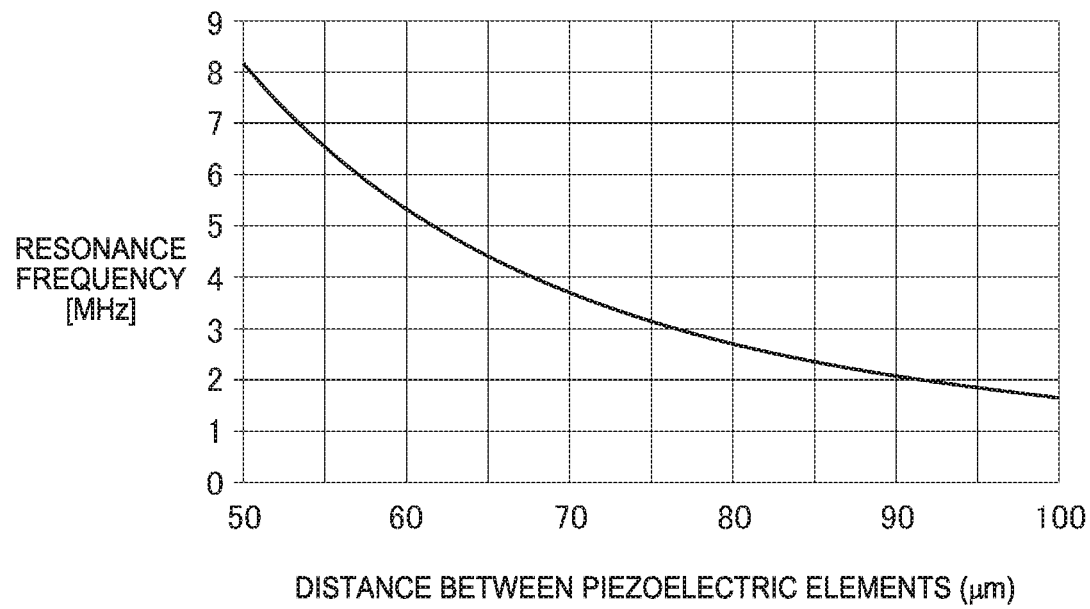
FIG. 7 is a diagram showing a relationship between a distance between piezoelectric elements adjacent to each other, and the resonance frequency of a vibrational region.

FIG. 7 is a diagram showing a relationship between the distance (the first dimension w) between the piezoelectric elements 22 adjacent to each other and the resonance frequency (the frequency of the ultrasonic wave output) of the vibrational region 23.

As shown in FIG. 7, the resonance frequency of the vibrational region 23 varies with the distance between the piezoelectric elements 22 adjacent to each other (i.e., the first dimension w as the width dimension of the vibrational region 23).

In the present embodiment, the piezoelectric elements 22 are arranged at regular intervals so that the distance between the piezoelectric elements 22 along the X direction and the distance between the piezoelectric elements 22 along the Y direction are both the first dimension w. Therefore, the resonance frequencies of the respective vibrational regions 23 become the same, and thus, as a result, the ultrasonic wave with the resonance frequency is output from the drive area Ar1. It should be noted that in the case in which the width dimension in the X direction of the vibrational region 23 and the width dimension in the Y direction thereof are different from each other, the resonance frequency of each of the vibrational regions 23 is determined by the width dimension in the short axis direction. For example, in the case in which the width dimension in the X direction of the vibrational region 23 is smaller than the width dimension in the Y direction thereof, the vibrational region 23 vibrates at the resonance frequency corresponding to the width dimension in the X direction, and thus, the ultrasonic wave with the resonance frequency is output.

Here, as shown in FIG. 6, the position (an area overlapping the piezoelectric element 22) at which the piezoelectric element 22 is disposed of the substrate 21 is larger in thickness dimension than the vibrational region not provided with the piezoelectric element 22, and further, the vibrational region 23 is provided with the slit grooves 231A, 231B. Therefore, the rigidity of the vibrational region 23 is lower compared to the area provided with the piezoelectric element 22 in the substrate 21. Therefore, the oscillation amplitude of the substrate 21 at the position where the piezoelectric element 22 is disposed becomes smaller than the oscillation amplitude of the vibrational region 23. Therefore, when driving the drive area Ar1, the ultrasonic wave with the resonance frequency of the vibrational region 23 is output with sound pressure corresponding to the oscillation amplitude of the vibrational region 23 as a result.

In other words, by setting the distance between the piezoelectric elements 22 based on such data of the relationship between the resonance frequency and the first dimension w as shown in FIG. 7, it is possible to obtain the piezoelectric film 2 capable of outputting the ultrasonic wave with a desired frequency.

Method of Manufacturing Piezoelectric Film 2

Then, a method of manufacturing such a piezoelectric film 2 as described above will be described.

Figure 8:
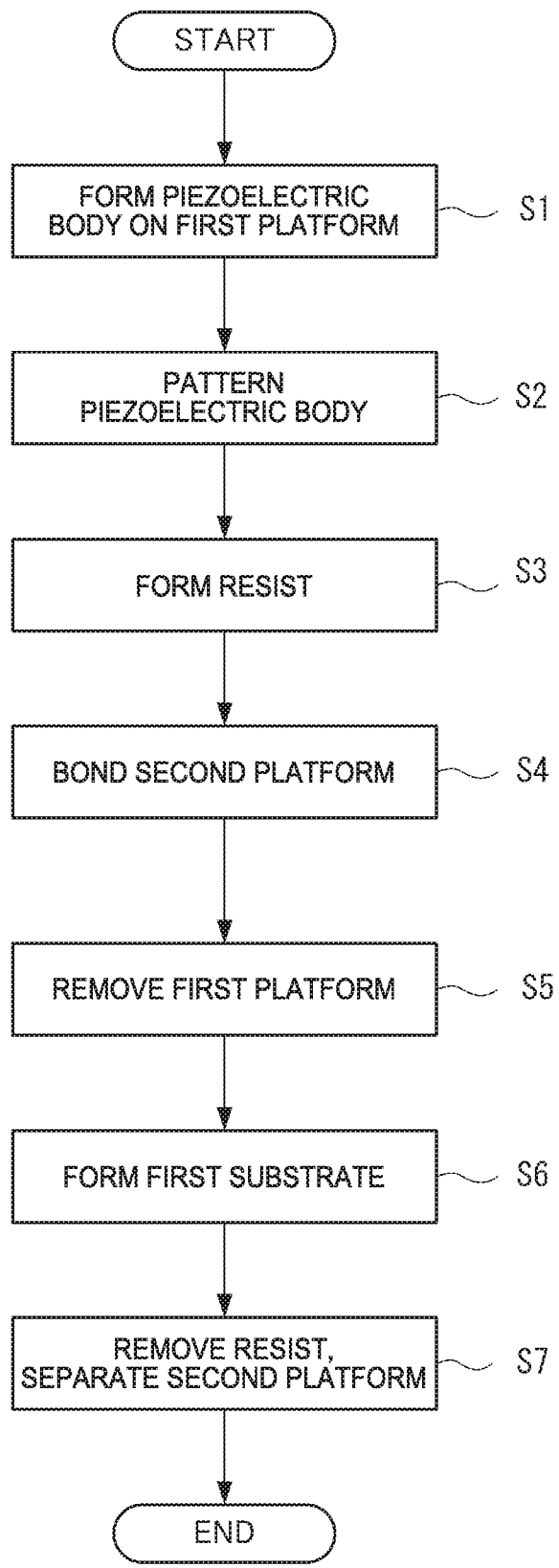
FIG. 8 is a flowchart showing a method of manufacturing the piezoelectric film according to the embodiment.
Figure 9:
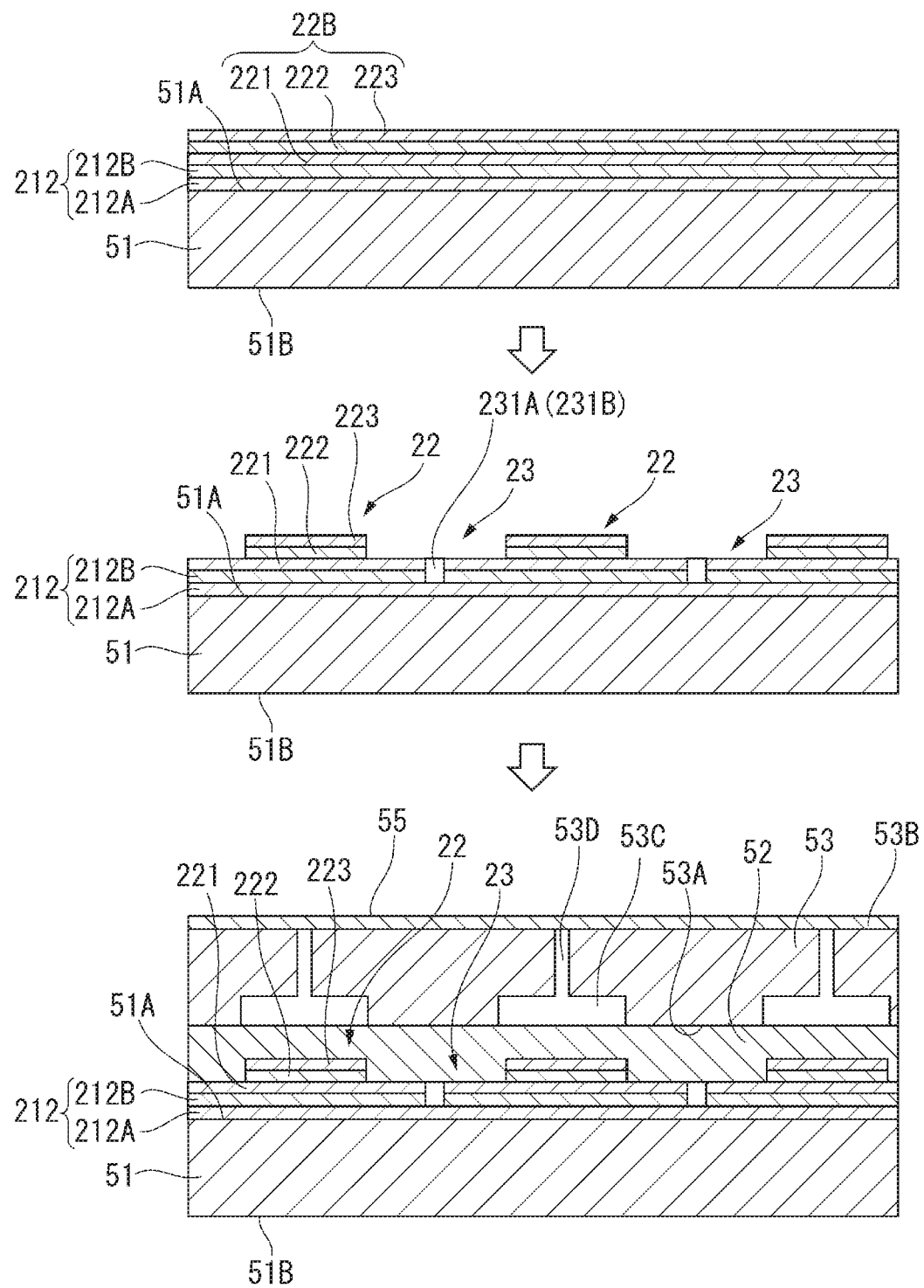
FIG. 9 is a diagram showing an outline of a process from the step S1 to the step S4 shown in FIG. 8.
Figure 10:
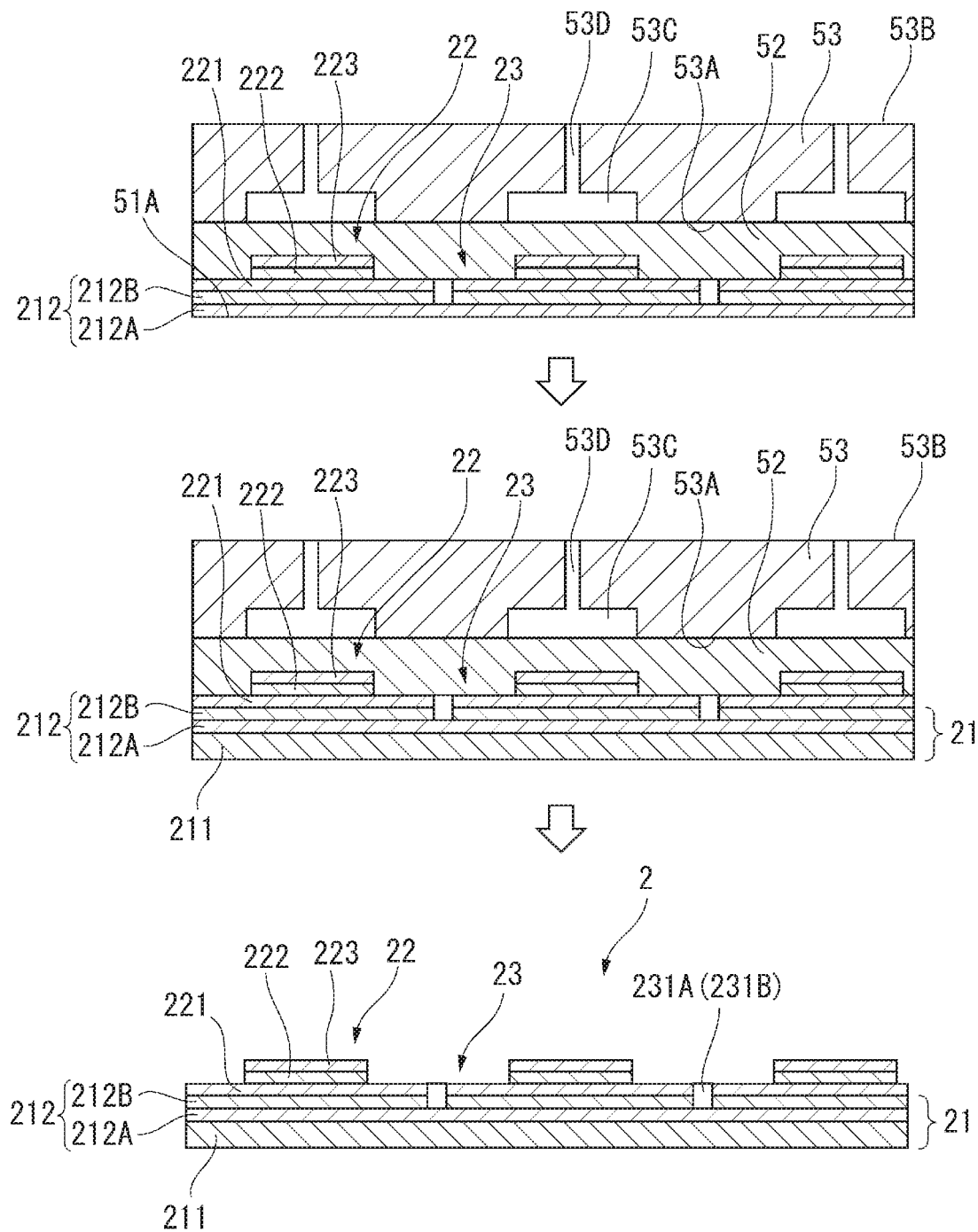
FIG. 10 is a diagram showing an outline of a process from the step S5 to the step S7 shown in FIG. 8.

FIG. 8 is a flowchart showing the method of manufacturing the piezoelectric film 2. FIG. 9 is a diagram showing an outline of a process from the step S1 to the step S4 shown in FIG. 8. FIG. 10 is a diagram showing an outline of a process from the step S5 to the step S7 shown in FIG. 8.

As shown in FIG. 8, in the case of manufacturing the piezoelectric film 2, a piezoelectric body 22B is formed on a first platform 51 on which the second substrate 212 is formed (step S1).

Specifically, as shown in the first drawing in FIG. 9, a thermal oxidation treatment is performed on one surface of the first platform 51 formed of an Si substrate to thereby form the $SiO_2$ layer 212A. It should be noted that the boundary surface of the first platform 51 with the $SiO_2$ layer 212A is defined as a first surface 51A, and a surface on an opposite side to the first surface 51A of the first platform 51 is defined as a second surface 51B. Subsequently, a Zr film is formed on the $SiO_2$ layer 212A, and then the Zr layer is thermal-oxidized to form the $ZrO_2$ layer 212B, namely the second substrate 212 constituted by the $SiO_2$ layer 212A and the $ZrO_2$ layer 212B is formed.

Then, the metal layers of Pt, Ti, Ir and Ti are formed on the surface of the second substrate 212 to form the first electrode film 221. Further, the piezoelectric film 222 is formed on the first electrode film 221. The piezoelectric film 222 can be formed using, for example, a solution growth technique, and by performing, for example, a coating process for applying a PZT solution on the first electrode film 221 and a calcination process for calcining the PZT solution thus applied a plurality of times, the piezoelectric film 222 is formed. Subsequently, the metal films of Ti and Ir are further stacked on the piezoelectric film 222 to form the second electrode film 223. Thus, as shown in the first drawing in FIG. 9, the second substrate 212 and the piezoelectric body 22B are formed on the first platform 51.

Subsequently, the piezoelectric body 22B and the second substrate 212 formed in the step S1 are patterned by etching and so on (step S2; a first process). Thus, as shown in the second drawing in FIG. 9, the piezoelectric elements 22 and the vibrational regions 23 are formed, and further, the slit grooves 231A, 231B are formed in each of the vibrational regions 23.

Then, a resist 52 for covering the piezoelectric elements 22 and the vibrational regions 23 is formed on the first surface 51A side of the first platform 51, namely on the second substrate 212 (step S3; a second process of the invention).

Further, a second platform 53 is bonded to a surface on an opposite side to the first platform 51 of the resist 52 so as to cover the resist 52 (step S4; a third process of the invention).

Here, the second platform 53 is an Si substrate having a third surface 53A on the resist 52 side and a fourth surface 53B on an opposite side to the third surface 53A. Further, in the second platform 53, the third surface 53A is provided with a plurality of recessed parts 53C, and is provided with through holes 53D each penetrating from the recessed part 53C to the fourth surface 53B. The recessed parts 53C are disposed at, for example, positions respectively overlapping the piezoelectric elements 22.

Further, in the step S4, a protective film 55 is formed on the entire area of the fourth surface 53B of the second platform 53.

Thus, as shown in the third drawing in FIG. 9, there is formed a structure in which the second substrate 212 and the piezoelectric elements 22 are sandwiched between the first platform 51 and the second platform 53.

After the process described hereinabove, the first platform 51 is removed from the second surface 51B side by performing a treatment such as polishing and an etching process in combination with each other (step S5; a fourth process in the invention). Thus, as shown in the first drawing in FIG. 10, the $SiO_2$ layer 212A of the second substrate 212 is exposed.

Subsequently, the first substrate 211 made of resin (e.g., polyimide) is formed on the $SiO_2$ layer 212A side of the second substrate 212 using, for example, a spin coat process (step S6; a fifth process of the invention). Thus, as shown in the second drawing in FIG. 10, the piezoelectric film 2 held by the second platform 53 is formed.

After the process described hereinabove, an etchant for removing the resist 52 is made to inflow into the recessed parts 53C through the through holes 53D of the second platform 53 to thereby remove the resist 52 (step S7; a sixth process). Thus, the resist 52 is removed, and by separating the second platform 53, there is formed such a piezoelectric film 2 as shown in the third drawing in FIG. 10.

Functions and Advantages of Present Embodiment

The piezoelectric film 2 according to the present embodiment is provided with the substrate 21 having flexibility, and the plurality of piezoelectric elements 22 disposed on the substrate 21 and arranged at the intervals of the first dimension w along the X direction (the first direction). Further, the piezoelectric elements 22 are each configured by stacking the first electrode film 221, the piezoelectric film 222 made of the inorganic material, and the second electrode film 223 along the Z direction (the thickness direction). Further, the area between the piezoelectric elements 22 adjacent in the X direction to each other of the substrate 21 constitutes the vibrational region 23 which can be displaced in the Z direction.

In such a piezoelectric film 2, when inputting the drive signal to the piezoelectric elements 22 at the same time, there occurs the vibration mode having the nodes in the vicinities of the end part positions of the piezoelectric element 22 and the antinode in the vibrational region 23 as shown in FIG. 6, and it is possible to output the ultrasonic wave due to the vibration of each of the vibrational regions 23. Therefore, unlike the related-art configuration of outputting the ultrasonic wave using the flexural vibration, the piezoelectric film 2 does not require the support body for regulating the frequency of the ultrasonic wave, and therefore, the rigidity of the substrate 21 can be made lower. Further, unlike the related-art configuration of outputting the ultrasonic wave using the thickness vibration, there is no need to change the thickness dimension of the piezoelectric elements 22 in accordance with the frequency, and therefore, there is no chance that the rigidity of the piezoelectric elements 22 increases depending on the frequency. Therefore, in the piezoelectric film 2 according to the present embodiment, it is possible to uniformly reduce the overall rigidity of the piezoelectric film 2 to thereby provide sufficient flexibility, and it is possible to freely deform the piezoelectric film 2 in accordance with the shape of the object 10.

Further, the piezoelectric film 2 according to the present embodiment uses the piezoelectric film 222 made of the inorganic material, and is therefore higher in piezoelectric characteristics, and higher in Curie point compared to the case of using the piezoelectric film made of an organic material such as PVDF. Therefore, even in the case of adopting, for example, a high temperature pipe as the object 10, there is no chance that the piezoelectric characteristics of the piezoelectric film 2 deteriorate, and it becomes possible to transmit the ultrasonic wave high in sound pressure from the piezoelectric film 2.

In other words, it is possible to obtain the piezoelectric film 2 high in piezoelectric characteristics and heat resistance, and also superior in flexibility.

The piezoelectric film 2 according to the present embodiment is provided with the slit grooves 231A each having an elongated shape along the Y direction at the center in the X direction of each of the vibrational regions 23 of the substrate 21. Similarly, the slit grooves 231B each having an elongated shape are each disposed along the X direction at the center in the Y direction of each of the vibrational regions 23.

By disposing such slit groove 231A, 231B, the vibrational regions 23 become easy to vibrate, and it is possible to amplify the oscillation amplitude. Thus, it is possible to output the ultrasonic wave high in sound pressure.

In the piezoelectric film 2 according to the present embodiment, three or more piezoelectric elements 22 are arranged along the X direction at the intervals of the first dimension w. Therefore, when inputting the drive signal to the piezoelectric elements 22, the vibrational region 23 between the piezoelectric elements 22 adjacent to each other vibrates as the antinode to output the ultrasonic wave. On this occasion, since the width dimensions of the vibrational regions 23 are the first dimension w, and are therefore the same dimension, the ultrasonic waves the same in frequency are respectively output from the vibrational regions 23. Therefore, it is possible to transmit the ultrasonic wave having a predetermined frequency at higher sound pressure from the piezoelectric film 2.

In the piezoelectric film 2 according to the present embodiment, the piezoelectric elements 22 are arranged along both of the X direction and the Y direction so as to form the roughly zigzag arrangement. In other words, in the case of defining the piezoelectric elements 22 arranged in the X direction as one element column 22A, there is adopted the configuration having the plurality of element columns 22A arranged along the Y direction. Further, the piezoelectric elements 22 constituting the element column 22A disposed (i+1)-th in the Y direction overlap the respective vibrational regions 23 in the element column 22A disposed i-th in the Y direction in the projection view along the Y direction. In other words, the piezoelectric elements 22 in the element columns 22A disposed at odd-numbered columns overlap each other in the Y direction, and the piezoelectric elements 22 in the element columns 22A disposed at even-numbered columns overlap each other in the Y direction. In contrast, the piezoelectric elements 22 in the element columns 22A disposed at the odd-numbered columns and the piezoelectric elements 22 in the element columns 22A disposed at the even-numbered columns fail to overlap each other in the Y direction.

By arranging the piezoelectric elements 22 of the piezoelectric film 2 as such a two-dimensional array structure as described above, the vibrational regions 23 adjacent in the X direction or the Y direction of the piezoelectric elements 22 to each other are vibrated at the same time in the case of driving the piezoelectric elements 22 at the same time, and it becomes possible to output the ultrasonic wave in a broad range from the drive area Ar1 (a two-dimensional area) of the piezoelectric film 2.

In the present embodiment, both of the width dimension in the X direction of each of the vibrational regions 23 and the width dimension in the Y direction thereof are set to the first dimension w. In other words, the distance between the piezoelectric elements 22 arranged in the X direction, and the distance between the piezoelectric elements 22 arranged in the Y direction become the same distance (the first dimension w). Therefore, it is possible to transmit the ultrasonic wave having the frequency corresponding to the first dimension w from each of the vibrational regions 23 on high power, and by combining the ultrasonic waves from the respective vibrational regions 23 with each other, it becomes possible to output the ultrasonic wave as a stronger sonic wave.

Further, in the present embodiment, the sum of the thickness dimensions of the piezoelectric element 22 and the second substrate 212 is equal to or lower than 5 µm. Therefore, the rigidity of the area of the piezoelectric film 2 where the piezoelectric elements 22 are disposed becomes lower, and it is possible to achieve further improvement of the flexibility of the piezoelectric film 2.

In the piezoelectric film 2 according to the present embodiment, the first electrode films of the plurality of piezoelectric elements 22 are connected to each other, and the second electrode films of the plurality of piezoelectric elements are connected to each other.

Therefore, when the voltage is applied between the single terminal section 221A corresponding to the first electrode film 221 of the piezoelectric film 2 and the single terminal section 223A corresponding to the second electrode film 223, the drive voltage is applied to all of the piezoelectric elements 22. Thus, as described above, it is possible to excite the vibration in the vibration mode having the antinodes in the vibrational regions 23, and it becomes possible to output the ultrasonic wave with the predetermined frequency from the piezoelectric film 2.

Modified Examples

It should be noted that the invention is not limited to the embodiment and the modified examples described above, but includes modifications and improvements within a range in which the advantages of the invention can be achieved, and configurations which can be obtained by arbitrary combinations of the embodiment and modified examples, and so on.

In the embodiment described above, there is illustrated the piezoelectric elements 22 arranged in the two-dimensional array structure in the drive area Ar1 of the piezoelectric film 2, but this is not a limitation. For example, it is also possible to adopt a piezoelectric film in which the piezoelectric elements are arranged at predetermined intervals in a one-dimensional array structure.

In the embodiment described above, there is shown an example in which the vibrational region 23 is provided with the slit grooves 231A, 231B, but it is not required to provide the slit grooves 231A, 231B. In this case, the rigidity of the vibrational regions 23 becomes lower than that of the area where the piezoelectric elements 22 are formed, and it is possible to increase the amplitude in the resonance.

Further, although there is illustrated the configuration in which the slit grooves 231A each having the elongated shape along the X direction and the slit grooves 231B each having the elongated shape along the Y direction cross each other to form the cross-like shape, this is not a limitation. For example, it is also possible to adopt a configuration in which a concave groove having a circular shape is disposed in a central part of each of the vibrational regions 23.

Further, besides such configurations provided with the slit grooves or the concave grooves, it is also possible to adopt a configuration in which the first electrode film 221 and the $ZrO_2$ layer 212B in the entire area overlapping the vibrational region 23 are removed.

In the embodiment described above, there is performed the process of removing the first platform 51 to keep the second substrate 212 in the step S5, but this is not a limitation. It is also possible to remove both of the first platform 51 and the second substrate 212. In this case, it is sufficient to directly form the first substrate 211 on the piezoelectric elements 22 and the first electrode film 221 held by the second platform 53.

In other words, the configuration in which the substrate 21 has the first substrate 211 and the second substrate 212 is adopted as the piezoelectric film 2, but the piezoelectric film 2 can also be formed only of the first substrate 211.

In the embodiment described above, there is adopted the configuration in which the first electrode films 221 of the respective piezoelectric elements 22 are connected to each other, and the second electrode films 223 of the respective piezoelectric elements 22 are connected to each other, and therefore, when applying the drive signal to the terminal sections 221A, 223A, the drive signal is input to all of the piezoelectric elements 22 at the same time, and thus the ultrasonic wave is output from the piezoelectric film 2. In contrast, it is also possible to adopt a configuration in which the piezoelectric elements are independent of each other, there are provided terminal sections corresponding respectively to the first electrode films 221 and the second electrode films 223 of the respective piezoelectric elements 22, and the terminal sections are connected to the control section 3.

In this case, the control section 3 controls the input timing of the drive signal to each of the terminal sections so that the drive signal is input to the piezoelectric elements 22 at the same time. Thus, it becomes possible to drive the piezoelectric film 2 in a similar vibration mode to that in the embodiment described above.

Besides the above, specific structures to be adopted when implementing the invention can be configured by arbitrarily combining the embodiment and the modified examples described above with each other, or can arbitrarily be replaced with other structures and so on within the range in which the advantages of the invention can be achieved.

The entire disclosure of Japanese Patent Application No. 2017-241520 filed Dec. 18, 2017 is expressly incorporated herein by reference.

What is claimed is:

1. A piezoelectric film comprising:
   a substrate having flexibility, the substrate including a first layer and a second layer that are laminated to each other; and
   at least two piezoelectric elements provided to the substrate so as to be arranged at intervals of a first dimension along a first direction, the at least two piezoelectric elements being directly adjacent to each other,
   wherein the at least two piezoelectric elements are each configured by stacking a first electrode film, a piezoelectric layer made of an inorganic material, and a second electrode film along a thickness direction of the substrate,
   an area of the substrate between the piezoelectric elements directly adjacent to each other along the first direction forms a vibrational region which can be displaced in the thickness direction, and
   a slit groove having a predetermined depth dimension along the thickness direction is disposed at a center of the vibrational region in the first direction of the substrate along a second direction intersecting the first direction, the slit groove penetrating the first layer and exposing an upper surface of the second layer.

2. The piezoelectric film according to claim 1, wherein the at least two piezoelectric elements are arranged along the first direction at intervals of the first dimension.

3. The piezoelectric film according to claim 1, wherein the at least two piezoelectric elements arranged along the first direction define an element column, and a plurality of the element columns are arranged along a second direction that intersects the first direction,
   the at least two piezoelectric elements in the element column disposed (i+1)-th in the second direction overlap respective vibrational regions disposed between the at least two piezoelectric elements in the element column disposed i-th in the second direction, and
   the at least two piezoelectric elements in the element column disposed (i+2)-th in the second direction overlap respective piezoelectric elements in the element column disposed i-th in the second direction.

4. The piezoelectric film according to claim 3, wherein i-th piezoelectric elements in the second direction and (i+2)-th piezoelectric elements in the second direction are arranged with a distance of the first dimension.

5. The piezoelectric film according to claim 1, wherein the substrate includes
   a first substrate made of resin, and
   a second substrate formed of the first layer and the second layer stacked on the first substrate, at least one of the first layer and the second layer including an oxide film,
   the at least two piezoelectric elements are provided to the second substrate, and
   a thickness in the thickness direction of the second substrate and the at least two piezoelectric elements is equal to or smaller than 5 µm.

6. The piezoelectric film according to claim 1, wherein first electrode films of a plurality of the piezoelectric elements are connected to each other, and
   second electrode films of a plurality of the piezoelectric elements are connected to each other.

7. A piezoelectric module comprising:
   the piezoelectric film according to claim 1; and
   a control section adapted to control the piezoelectric film.

8. A piezoelectric module comprising:
   the piezoelectric film according to claim 2; and
   a control section adapted to control the piezoelectric film.

9. A piezoelectric module comprising:
   the piezoelectric film according to claim 3; and
   a control section adapted to control the piezoelectric film.

10. A piezoelectric module comprising:
    the piezoelectric film according to claim 4; and
    a control section adapted to control the piezoelectric film.

11. A piezoelectric module comprising:
the piezoelectric film according to claim 5; and
a control section adapted to control the piezoelectric film.

12. A piezoelectric module comprising:
the piezoelectric film according to claim 6; and
a control section adapted to control the piezoelectric film.

13. The piezoelectric module according to claim 7, wherein
the control section inputs a predetermined drive signal to a plurality of the piezoelectric elements at a same timing.

* * * * *